(12) United States Patent
Tatnell

(10) Patent No.: US 11,696,969 B2
(45) Date of Patent: Jul. 11, 2023

(54) ETHYLENE OXIDE TREATMENT INDICATOR, LABEL AND METHOD OF USE

(71) Applicant: Global Life Sciences Solutions Operations UK Ltd, Sheffield (GB)

(72) Inventor: Peter James Tatnell, Cardiff (GB)

(73) Assignee: Global Life Sciences Solutions Operations UK Ltd, Sheffield (GB)

(*) Notice: Subject to any disclaimer, the term of this patent is extended or adjusted under 35 U.S.C. 154(b) by 579 days.

(21) Appl. No.: 16/078,749

(22) PCT Filed: Feb. 28, 2017

(86) PCT No.: PCT/EP2017/054587
§ 371 (c)(1),
(2) Date: Aug. 22, 2018

(87) PCT Pub. No.: WO2017/148908
PCT Pub. Date: Sep. 8, 2017

(65) Prior Publication Data
US 2019/0046678 A1    Feb. 14, 2019

(30) Foreign Application Priority Data
Feb. 29, 2016   (GB) ..................................... 1603462

(51) Int. Cl.
*A61L 2/28*     (2006.01)
*A61L 2/20*     (2006.01)
*G01N 31/22*    (2006.01)

(52) U.S. Cl.
CPC .................. *A61L 2/28* (2013.01); *A61L 2/206* (2013.01); *G01N 31/226* (2013.01); *A61L 2202/23* (2013.01); *A61L 2202/24* (2013.01)

(58) Field of Classification Search
None
See application file for complete search history.

(56) References Cited

U.S. PATENT DOCUMENTS

| | | |
|---|---|---|
| 3,258,312 A | 6/1966 | Olson |
| 4,095,642 A | 6/1978 | Sumimoto et al. |
| 4,206,844 A | 6/1980 | Thukamoto et al. |
| 6,395,551 B1 | 5/2002 | Kipke et al. |
| 2002/0012610 A1 | 1/2002 | Dufresne et al. |

(Continued)

FOREIGN PATENT DOCUMENTS

| | | |
|---|---|---|
| CN | 1367384 A | 9/2002 |
| GB | 2219084 A | 11/1989 |

(Continued)

OTHER PUBLICATIONS

PCT International Search Report and Written Opinion for PCT Application No. PCT/EP2017/054587 dated May 18, 2017 (9 pages).

(Continued)

*Primary Examiner* — Lore R Jarrett
(74) *Attorney, Agent, or Firm* — Eversheds Sutherland (US) LLP

(57) ABSTRACT

The present invention provides an indicator useful in confirming successful sterilisation and/or nucleic acid decontamination by ethylene oxide (EtO) treatment. The invention also provides a label comprising said indicator and methods for use of the indicator and label in a method of EtO treatment.

11 Claims, 4 Drawing Sheets

(56) References Cited

U.S. PATENT DOCUMENTS

| | | | |
|---|---|---|---|
| 2003/0211618 A1* | 11/2003 | Patel | A61L 2/28 436/38 |
| 2003/0235654 A1* | 12/2003 | Puntambekar | A61L 2/206 106/31.28 |
| 2005/0278012 A1 | 12/2005 | Vonderwalde | |
| 2011/0158917 A1 | 6/2011 | MacDonald et al. | |
| 2012/0083423 A1* | 4/2012 | Auger | C07K 14/81 435/7.1 |
| 2014/0000392 A1* | 1/2014 | Harvey | B01L 3/505 73/864.91 |

FOREIGN PATENT DOCUMENTS

| | | |
|---|---|---|
| JP | 2002323451 A | 11/2002 |
| WO | 01/10471 A1 | 2/2001 |
| WO | 0110471 A1 | 2/2011 |

OTHER PUBLICATIONS

GB Search Report for GB Application No. 1603462.1 dated Jul. 27, 2016 (5 pages).
European Office Action for corresponding EP Application No. 17707851.6, dated Feb. 24, 2023 (5 pages).

* cited by examiner

ETHYLENE OXIDE TREATMENT INDICATOR, LABEL AND METHOD OF USE

CROSS REFERENCE TO RELATED APPLICATIONS

This application claims the priority benefit of PCT/EP2017/054587 filed on Feb. 28, 2017 which claims priority benefit of Great Britain Application No. 1603462.1 filed Feb. 29, 2016. The entire contents of which are hereby incorporated by reference herein.

TECHNICAL FIELD OF THE INVENTION

The present invention relates to products and processes useful in sterilisation and/or nucleic acid decontamination. In particular the present invention provides an indicator useful in confirming successful sterilisation and/or nucleic acid decontamination by ethylene oxide (EtO) treatment. Also provided by the invention is a label comprising said indicator and methods for use of the indicator and label in a method of EtO treatment.

DESCRIPTION OF RELATED ART

Sterilising in the provision of medical services and in the food industry is a vital process where the absence of potentially pathogenic microorganisms such as bacteria, viruses, spores, protozoa and fungi is key for safety. Furthermore, in analytical science and in particular in forensic science, biological contamination leading to false results must be avoided. The aim of sterilisation is that any pathogenic organisms are altered so that reproduction is no longer possible. For devices and disposable articles or items that are used for analysis of nucleic acids, in particular for polymerase chain reaction (PCR) applications, sterility is not enough, because even dead pathogenic organisms may still have amplifiable DNA or RNA molecules.

A known technique for sterilisation comprises exposure to ethylene oxide (EtO). This technique can be used in place of steam sterilisation for devices that incorporate electronic components and for thermally unstable materials, neither of which can support conventional high temperature steam sterilisation. As a further advantage, EtO is capable of reaching and sterilising devices surrounded by gas-permeable packing materials. EtO acts upon biological material through alkylation producing irreversible damage to nucleic acids, proteins and enzymes thereby leading to a prevention in further reproduction and sterilisation. EtO treatment can also enable complete inactivation (i.e. decontamination) of nucleic acid.

The effectiveness of EtO treatment for sterilisation is traditionally monitored with biological indicators that are composed of the microorganism *Bacillus atrophaeus*, usually inoculated onto a 1.5×0.25 inch paper carrier, an example of which is the Spordex (STERIS) bacterial test strip. For routine monitoring purposes, the biological indicators are placed throughout the load, which is exposed to EtO and sterilised. Subsequently, the biological indicators are removed and forwarded to a centralised testing laboratory, where they are placed into a Bacillus growth medium and grown for 7 days (according to the United States Pharmacopeia, 37th edition, 2014). After the incubation period, negative Bacillus growth demonstrates that the sterilisation process was effective. The load may then be considered as sterile and therefore ready for release to market, provided all other release criteria such as the removal of EtO etc. are met. When using this traditional biological indicator monitoring method of the EtO sterilisation process, expenses are incurred in two ways. First, there is the expense of the biological indicators and the associated laboratory testing; and secondly, there is a large amount of capital tied up in the inventory which must be held in quarantine until after the laboratory testing is complete. In addition to the expense, the use of biological indicators may increase the risk due to the possible of contamination of the indicator while being handled at the testing laboratory etc. or even the post contamination of the product post EtO treatment. In most cases, a failure of a biological indicator, even though laboratory induced, would be considered a sterility failure and result in the requirement for reprocessing of all of the materials which were contained in the steriliser load. For DNA-free status costs are incurred based upon molecular-based QC tests and quarantine costs are also applicable.

As an alternative, chemical indicators that respond by changing colour on exposure to EtO are useful to monitor the effectiveness of the EtO sterilisation process. U.S. Pat. No. 2,998,306 teaches acid-alkali indicator dyes for use as visual indicators that a required concentration of EtO has been applied for a necessary time to ensure sterilisation. U.S. Pat. No. 2,998,306 teaches that bromophenol blue and methyl red are particularly useful as they change colour sharply when an acid solution approaches pH 7. In a more recent publication, U.S. Pat. No. 6,800,124, advantageous EtO sterilisation indicator inks include the pH indicator dyes Bromocresol green, Bromophenol blue, Methyl red, Ethyl orange, and combinations thereof. Chemical indicators such as these are commercially-available available from e.g. Medovation, Getinge, (Australia Pty. Ltd), Namsa, PMA SteriRITE etc.

There is scope for alternative dyes for use as indicators of EtO treatment that are both compatible with cellulose-based papers and do not interfere with DNA amplification methods.

SUMMARY OF THE INVENTION

In a first aspect the present invention provides an indicator for confirming successful ethylene oxide (EtO) exposure wherein said indicator comprises a solid support treated with a dye selected from the group comprising:
 (a) Bromophenol red
 (b) Bromothymol blue
 (c) Bromoxylenol blue
 (d) Chlorophenol red
 (e) m-Cresol purple
 (f) Cresol red
 (g) Neutral red
 (h) Nile blue
 (i) Rosolic acid
 (j) Fast violet B
 (k) Mordant blue 9
 (l) Oil red O
 (m) Phthalocyanine Cu
 (n) Phthalocyanine green
 (o) Phthalocyanine Fe
 (p) Phthalocyanine Mg
 (q) Phthalocyanine Zn
 (r) Prussian blue
 (s) Ruthenium red In a second aspect the present invention provides a label for attachment to an article intended for EtO treatment wherein said label comprises the indicator as defined herein and means to fix said indicator to said article.

In a third aspect the present invention provides a method to confirm successful EtO exposure wherein said method comprises:
(a) exposing an article to EtO for a defined period of time wherein said article comprises the indicator of the first aspect of the invention or the label of the second aspect of the invention;
(b) inspecting the colour of said indicator following step (i).

In a fourth aspect the present invention provides for use of the indicator of the first aspect of the invention or the label of the second aspect of the invention to confirm successful EtO exposure.

In a fifth aspect the present invention provides a kit for carrying out the method of the third aspect of the invention wherein said kit comprises the indicator of the first aspect of the invention or the label of the second aspect of the invention.

The dyes used in the present invention are shown to be compatible with cellulose-based papers thereby facilitating a convenient manufacturing process. Furthermore it is demonstrated that the dyes of the present invention do not interfere with DNA amplification methods. The various indicator of the present invention is therefore useful in sterilisation processes as well as in nucleic acid decontamination.

DETAILED DESCRIPTION OF THE PREFERRED EMBODIMENTS

Figure 1A:
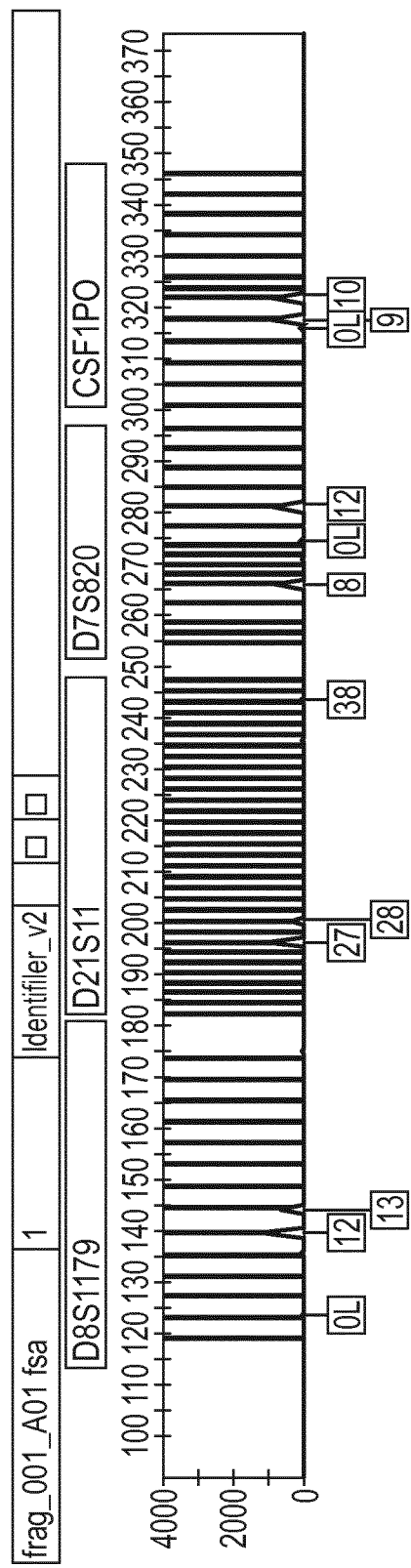
FIGS. 1a-d show an example electrophoretogram of STR products derived a solid support that had been dyed using Chlorophenol red. The STR profile is derived from a HeLa cell sample. The results indicate the potential for correlating a colour change of a dye post-EtO exposure with the generation of a STR profile.

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The first aspect of the present invention provides an indicator for confirming successful ethylene oxide (EtO) exposure wherein said indicator comprises a solid support treated with a dye.

The term "indicator" used herein means a device that produces a clear colour change upon exposure to EtO treatment for sterilisation and/or nucleic acid decontamination.

The colour change that indicates the desired end point (i.e. sterilisation or DNA contamination) does not necessarily have to be the complete colour change, e.g. for a dye that changes from blue to red, an "incomplete" colour change to purple may indicate that the EtO treatment has achieved the aim of sterilisation and/or nucleic acid decontamination.

The term "successful" as used in connection with EtO exposure refers in the present invention to wherein said exposure results in elimination of viable microorganisms, e.g. from a medical device or consumable, or removal of contaminating nucleic acid, e.g. DNA or RNA from a sample collection product or device.

In one embodiment wherein nucleic acid decontamination is DNA decontamination, the term "DNA-free" can be defined as no more than 20 pg DNA, which is based upon minimum detection limits for biological samples applied to solid support materials and then subjected to short tandem repeat (STR) profiling. STR involves the amplification of specific alleles at defined loci in the human genome for human identification purposes. It is associated with multiplex PCR and the resultant fluorescently labelled PCR products are separated by capillary electrophoresis (CE). The definition of DNA-free status may be derived from using the Promega PowerPlex 18D kit a product is certified as DNA-free providing that no more than two STR PCR products are generated that are greater than 50 RFU (relative fluorescent units) values when using an Applied Biosystems 3130 xl Genetic Analyser. The publications by Archer et al. (Forensic Science International: Genetics 4 (2010) 239-243) and Shaw et al. (Int J Legal Med (2008) 122:29-33) provide more detail on methods for nucleic acid decontamination.

The term "solid support" can in certain embodiments be understood to comprise a glass- or silica-based solid phase medium, a plastics-based solid phase medium, porous ceramics or a fibrous material. In one embodiment said glass-based solid phase medium is selected from glass, glass fibre and glass microfiber. In one embodiment said silica-based solid medium is selected from silica, silica gel and silica oxide. In one embodiment said fibrous material is selected from cellulose, nitrocellulose, wool and carboxymethylcellulose. In one embodiment said plastics-based solid medium is selected from polyester, polyamide, carbohydrate polymers, polypropylene, polytetrafluororethylene and polyvinylidinefluoride. In one embodiment said solid support comprises a fibrous material selected from cellulose fibres; or alginates; or fibrous polymeric materials.

In one embodiment said solid support is selected from the group comprising cellulose based paper, woven or non-woven fibrous materials, including man made, or naturally occurring polymer fibres such as an alginate, mineral fibre based materials such as glass fibre materials.

In one embodiment said solid support is a cellulose based paper.

The phrase "treated with a dye" used in connection with the solid support of the invention refers to wherein the dye forms a chemical bond with the solid support.

In one embodiment said solid support is chemically impregnated with said dye.

In one embodiment said solid support is coated with said dye.

In one embodiment said dye is covalently attached to said solid support.

In one embodiment said dye is selected from Bromophenol Red, Bromocresol Purple, Bromothymol Blue, Bromoxylenol Blue, Chlorophenol Red, m-Cresol Purple, Cresol Red, Neutral Red, Nitrazine Yellow, Rosolic Acid, Mordant Blue 9 and Ruthenium Red.

In one embodiment said solid support comprises more than one of said dyes.

In one embodiment said solid support further comprises one or more nucleic acid stabilisation chemicals.

In one embodiment said solid support is impregnated with said nucleic acid stabilisation chemicals.

In one embodiment said solid support is coated with said nucleic acid stabilisation chemicals.

In one embodiment said nucleic acid stabilisation chemicals are covalently attached to said solid support.

In one embodiment said nucleic acid stabilisation chemicals are selected from the group comprising a weak base, a chelating agent, an anionic surfactant, an anti-oxidant.

In one embodiment said weak base is Tris HCl.

In one embodiment said chelating agent is EDTA.

In one embodiment said an anionic surfactant is SDS.

In one embodiment said anti-oxidant is uric acid.

In one embodiment said nucleic acid stabilisation chemicals are Tris HCl, EDTA, SDS and uric acid. A commercially-available version of a solid support including all these chemicals is FTA.

In one embodiment said one or more nucleic acid stabilisation chemicals comprises a chaotrope.

In one embodiment said chaotrope is a guanidinium salt.

In one embodiment chaotrope is guanidine hydrochloride. A commercially-available version of a solid support comprising guanidine hydrochloride is FTA™ Elute (GE Healthcare).

The second aspect of the present invention is a label for attachment to an article intended for EtO treatment wherein said label comprises the indicator as defined herein and means to fix said indicator to said article.

In one embodiment said means to fix said indicator comprises adhesive applied to one surface of said solid support.

In one embodiment said adhesive is a glue.

The third aspect of the present invention is a method to confirm successful EtO exposure.

The term "successful" is as defined hereinabove in relation to the first aspect of the invention.

The term "exposing" in connection with EtO means placing the article in contact with EtO under conditions suitable for the EtO to interact with said article resulting in sterilisation and/or decontamination. The person skilled in the art will be well acquainted with the conditions required in using EtO for these purposes (see e.g. Chapter 6 of "Disinfection and Decontamination" 2008 CRC Press; Gurusamy Manivannan, Ed. And Chapter 4 of "Advanced Topics in Forensic DNA Typing: Methodology" 2012 Elsevier; John M. Butler, Ed.).

The term "defined period of time" refers to a period of time selected as being sufficient to result in sterilisation and/or nucleic acid decontamination.

The term "comprises the indicator" can be taken to encompass wherein the article is the indicator and also wherein the indicator is affixed to or associated with said article, wherein "associated with" can mean that the indicator is present alongside the article during EtO exposure.

In one embodiment where the article is the indicator non-limiting examples of the type of articles encompassed include sample collection cards, membrane-based collection devices, swabs, plastic items such as Easi-collect devices.

The term "inspecting" means visual inspection for a change in the colour of the indicator.

In one embodiment said defined period of time is 3-6 hours.

In one embodiment said defined period of time is suitable for nucleic acid decontamination.

In one embodiment the method of the invention may be used as a quality control (QC) test based on molecular amplification of DNA. In current routine practice such a QC test would be based on STR profiles based on peak analysis. Where the peaks are below a particular threshold the DNA is deemed to be an artefact (i.e. non-amplifiable). Application of the present invention as an alternative to this current method provides a more straightforward and faster QC process.

In one embodiment said defined period of time is suitable to sterilise said article.

In one embodiment said article is a medical, pharmaceutical or healthcare article.

In one embodiment said article is a consumable.

In one embodiment said consumable is selected from the list comprising cotton swabs, latex gloves and micro test tubes.

In one embodiment said article is packed into an EtO-permeable container.

In one embodiment said EtO-permeable container is a gas-permeable bag.

The exposing step can be carried out using methods known to those of skill in the art. Non-limiting examples are described by Archer et al. (2010 Forensic Sci Intl: Genetics; 4: 239-243) and Shaw et al. (2008 Int J Legal Med; 122: 29-33) and in US20070148035.

In one embodiment said exposing step comprises:
(i) sealing said article within an interior space of a temperature-controlled pressure chamber,
(ii) adjusting the pressure within the interior space of said chamber,
(iii) increasing the temperature of the interior space,
(iv) introducing EtO into said interior space and in contact with said surface,
(v) incubating the article in the present of the ethylene oxide for a predetermined length of time,
(vi) rinsing said article with cleaning gas, and
(vii) desorbing the ethylene oxide.

In one embodiment said exposing step comprises:
(i) sealing said article within an interior space of a temperature-controlled pressure chamber,
(ii) humidifying the interior,
(iii) adjusting the pressure within the interior space of said,
(iv) introducing ethylene oxide into said interior space and in contact with said surface,
(v) incubating the article in the presence of the ethylene oxide for a predetermined length of time,
(vi) rinsing said article with a cleaning gas, and
(vii) desorbing the ethylene oxide.

In certain embodiments of the above-described exposing steps the pressure is adjusted to about 40-800 mbars, about 100-800 mbars, about 200-600 mbars or about 400-500 mbars.

In certain embodiments of the above-described exposing steps the temperature is about 30-60° C., 35-55° C. or 40-50° C.

In certain embodiments of the second of the above-described exposing steps humidifying is to a relative humidity is about 50-90%, about 55-80% or about 60-75%.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

Brief Description of the Examples Example 1 describes the list of dye candidates.
Example 2 describes the initial paper dyeing tests carried out.
Example 3 describes the colour change on exposure to ethylene oxide of the candidate dyes.
Example 4 describes STR analysis of biological samples applied to indicators of the present invention.

List of Abbreviations Used in the Examples

DNA deoxyribonucleic acid
EtO ethylene oxide
STR short tandem repeat
PCR polymerase chain reaction

EXAMPLES

Example 1

List of Dye Candidates

A list of over 300 potential candidate dyes was produced. These included those that were believed to function as pH, chromatographic and/or biological indicating dyes respectively. Within the set of chromatographic dyes there were subsets of different dye types including food colourings, inorganic dyes and fluorescent dyes. The set of biological indicating dyes included DNA specific fluorescent dyes and stains for use with phospholipids, proteins etc. The extensive list of dyes was reduced to 49 (see Table 1 in the Figures section) by eliminating dyes that:
  were toxic or harmful
  would not give a suitable colour on paper
  were insoluble in water
  were highly fluorescent which would affect potential downstream applications
  would need visual aids such as ultra violet lighting
  would have a pH colour change range not supportive of biological samples
  were known to have poor stability or be light sensitive
  required complex manufacturing procedures Example 2 Initial Paper Dyeing Tests Aqueous-based solutions were made up of all the candidate indicating dyes. Water-based solutions were considered as this is the preferred method for large scale manufacture when chemically coating/impregnating sample collection cards. The dyes were applied to several cellulose-based papers including chemically coated, chemically impregnated and non-coated papers. The solutions for the pH indicating dyes were adjusted depending upon the existing chemical coating so that when applied the correct pH levels were present thereby ensuring that the correct dye colour was maintained. The solution was placed in a petri dish and small pieces of each paper were dipped into the solution using a pair of forceps for a few seconds, ensuring an even coating. The dyed papers were then allowed to dry at ambient temperature overnight.

At this stage it was possible to rule out several candidate dyes based on either poor solubility, poor colour after drying and/or issues with drying. This suggests that they are not ideally suited for either large scale manufacture or use as indicating dyes on paper. These included the following; Nile Blue (13), Oil Red O (38), Phthalocyanine Cu (40), Phthalocyanine Green (41), Phthalocyanine Fe (42), Phthalocyanine Mg (43), Phthalocyanine Zn (44) and Prussian Blue (45).

The dyes Brilliant Blue E133 (16), Fast Green E143 (17), Fast Violet B (33) and indocyanine Green (35) all exhibited a non-optimal colour when applied to the cards.

Example 3 Candidate Dyes—Colour Change on Exposure to Ethylene Oxide

Paper sheets coated with the remaining candidate dyes were generated and subjected to EtO to identify those that exhibited a colour change and thereby potentially may function as a chemical indicator for EtO exposure.

Cellulose-based paper sheets were cut up into 4×6 cm pieces. Aqueous solutions of each dye were prepared as described earlier. Appropriate volumes of the dye solutions were dispensed in petri dishes and the cut papers were placed for a few seconds in the solution using forceps. The dyed papers were subsequently allowed to dry overnight on aluminium foil at ambient temperature. A protective sheet of aluminium foil was place on top to protect the dyed papers from potential contamination, light etc. Chemical names/numbers were added to facilitate identification. After drying, the dyed papers were attached to larger A4 pieces of card producing sample sheets. Images were taken of each sample sheet. Multiple sample sheets were generated for each paper type. Controls sheets were also generated and these were stored in envelopes at ambient temperature covered with protective aluminium foil. Several of the cellulose papers were also coated with additional chemicals that provide for the long term storage of nucleic acids. These additional chemicals are those associated with the commercially-available FTA™ product range from GE Healthcare.

Cellulose papers coated with the chemical indicator dyes were forwarded to Synergy Health Sterilisation UK Ltd for exposure to EtO. EtO Cycle conditions were based upon those described by Archer et al., Forensic Sci. Intl: Genetics 4, 2010, p 239-243 and Shaw, et al Int. J. Legal Med., 2008, 122, p 29-33. Actual EtO cycling conditions used were: Cycle 1, pre-conditioning at 42.0-45.0° C., for 12 h at a relative humidity 64.5-72.8%. EtO sterilisation was carried out at 43.7-46.5° C. for 4 h at 480 mbar. Removal of EtO was achieved by de-gassing at 42.2-46.2° C. for 12 h. Cycle 2; pre-conditioning at 43.6-47.7° C. for 12 h, at a relative humidity of 64.7-72.8%. EtO sterilisation; 44.1-46.7° C. for 4 h at 480 mbar. De-gassing was performed at 43.0-46.2° C. for 12 h. The colour of samples exposed to EtO were compared to the control samples to determine if any colour changes and/or fading had occurred.

Dye samples that showed little or no colour change and therefore displayed good stability/resistance to EtO treatment were as described below. These dyes were subsequently discounted from the study.

| | | |
|---|---|---|
| 01 Alizarin Red S | 02 Bromocresol Purple | 03 Bromophenol Blue |
| 10 Litmus Soln | 11 Methyl Red | 16 Brilliant Blue E133 |
| 17 Fast Green FCF E143 | 18 Allura Red AC E129 | 19 Acid Red 1 |
| 20 Erioglaucine | 21 Ponceau S Soln | 22 Tartrazine |
| 23 Direct Blue 71 | 24 Direct Red 23 | 25 Direct Violet 51 |
| 26 Acid Red 4 | 27 Alcian Blue 8GX | 28 Brilliant Blue G |

-continued

| 29 Bromocresol Green | 30 Chlorazol Fast Pink | 31 Coomassie Brilliant Blue R |
|---|---|---|
| 32 Crocein Orange | 34 Indigo Carmine | 35 Indocyanine Green |
| 36 Methylene Blue | 39 Orange G | 46 Reactive Blue 4 |
| 47 Rhodamine B | 48 Rhodamine 6G | |

The following dyes exhibited discolouration when exposed to EtO;

Bromophenol Red (4) when exposed to EtO darkened slightly to a deep blue colour and to greenish brown when applied to chemically coated papers and uncoated papers respectively. Nitrazine Yellow (14) and Mordant Blue 9 (37) did not show any significant colour change when applied to uncoated papers exposed to EtO but were discoloured when applied to chemically-coated papers (data not shown).

The remaining dye samples showed significant colour change/fading, for example Chlorophenol Red (7) changed from purple to yellowish brown on uncoated papers and to a red on chemically coated paper. M-Cresol Purple (8) changed from dark purple to yellow when applied to both coated and uncoated papers exposed to EtO.

These tests show that the majority of the dyes (29/40) were resistant to EtO treatment under the dual cycle conditions used and did not exhibit any significant colour change. The remaining dyes were all affected by EtO treatment and thereby exhibited a change in colour. These latter dyes are therefore capable of functioning as chemical indictors that confirm exposure to EtO and subsequently DNA-free status.

Example 4 STR Analysis of Biological Samples Applied

In order to demonstrate the potential for correlating a colour change post EtO exposure with DNA-free status the following experiment was performed. HeLa cells applied to cellulose-papers dyed with chlorophenol red were used to test the compatibility of the candidate dyes with short tandem repeat (STR) analysis. This was used to related DNA levels via STR profiles to the presence of an indicator dye that changes colour on exposure to EtO. Chlorophenol red was applied directly to both chemically-coated and uncoated papers.

Sample preparation—Chlorophenol red was dissolved in 0.1 M Tris HCl pH 8.0 and the solution was applied to 4×6 cm pieces of chemically-coated cellulose paper and allowed to dry overnight on the bench. Hela cells (40 µl) in TE buffer, pH 7.8 (concentration ~$2.5×10^5$ cells per ml) were pipetted onto a sterile foam applicator and applied to the dyed paper sample using mild pressure for ca. 10 s. STR PCR reactions were set-up using AmpFL STR® Identifier® PCR Amplification Kit (ABI) as per user manufacturer's instructions. Punches (1.2 mm) were taken from controls and chemically coated dyed papers and subjected to STR profiling. Two replicates were performed for each of the samples including two positive controls on Indicating FTA™ micro-cards. PCR was performed using GeneAmp® PCR System 9700 as per user manufacturer's instructions (28-cycle PCR). PCR products were separated by CE using 3130 xl Genetic Analyzer (ABI) and analysed using GeneMapper™ v3.2 software.

Figure 1B:
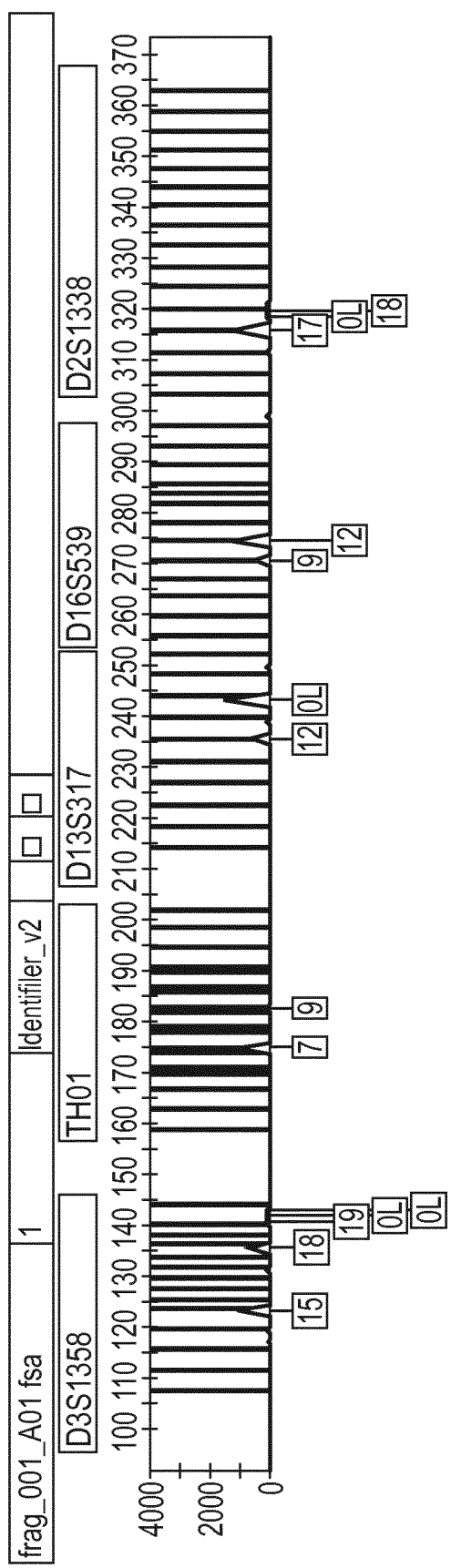
Figure 1C:
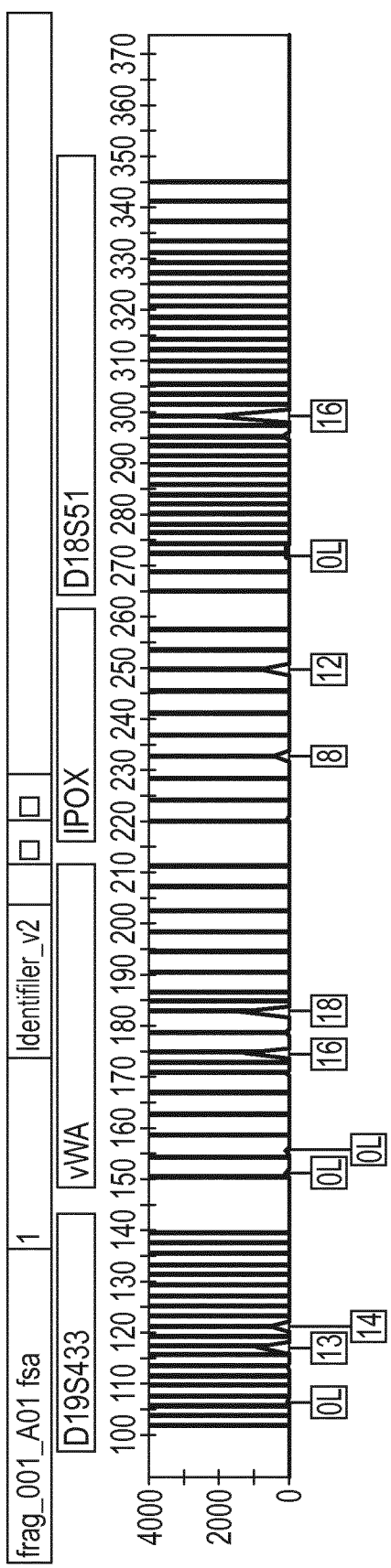
Figure 1D:
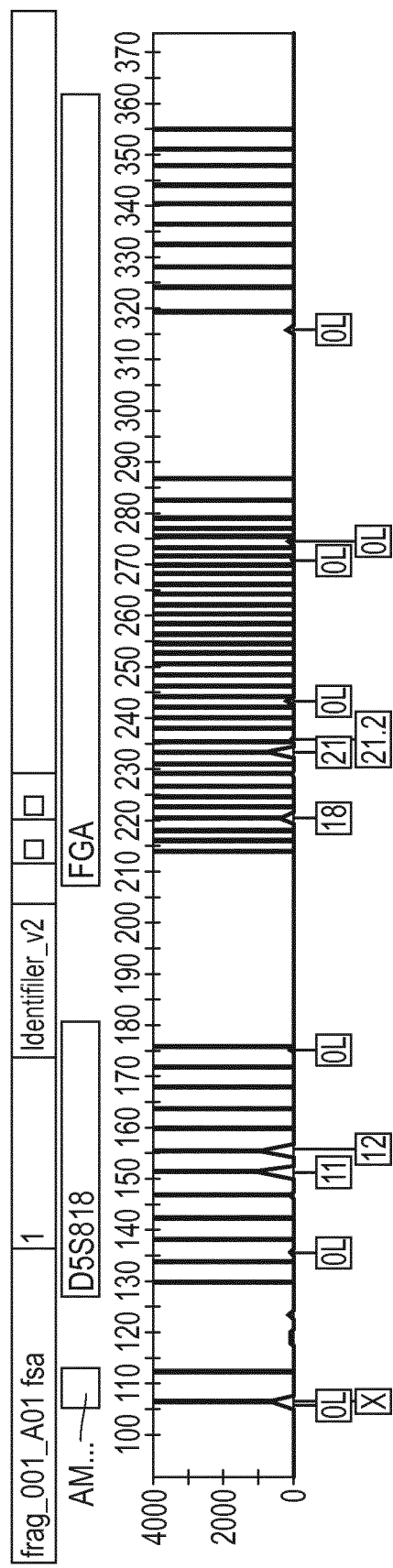

All the samples tested produced concordant allelic designation that was comparable to control samples (see FIGS. 1a-d). The chlorophenol red dyed samples generated full profiles with comparable peak height and peak balance to the controls. Some variability in the data was observed and this was attributed to the known heterogeneous challenge of applying biological samples to solid support materials. Similar variability was observed from samples applied to the controls. See Oostdik et al. 2013 Forensic Sci Int Genet; 7(1): 129-135.

The composite mean peak heights derived from all the solid support were in excess of that require for uploading STR profiles to National DNA databases, indicating that the presence of the dye on the solid support had negligible interference or inhibitory effects (data not shown). The amplification efficiency of the multiplex STR PCR is demonstrated by the minimal amount of PCR product tail off. STR profiles derived from dyed samples generate comparable peak heights and comparable tail off rates compared to controls (data not shown).

These data indicates that the presence of the chlorophenol red applied to the solid supports did not significantly affect the quality of the resultant STR profiles. The chlorophenol red changed colour when exposed to EtO and therefore this study demonstrates that a colour change in the dye can be correlated to the presence of DNA on a solid support as determined by using HeLa cells and STR profiling.

TABLE 1

| No | Dye Name | Dye Type | Other |
|---|---|---|---|
| 01 | Alizarin Red S | pH dye | pH 3.7 (yellow) pH 5.2 (purple), anionic anthraquinone dye |
| 02 | Bromocresol Purple | pH dye | pH 5.2 (yellow) pH 6.8 (purple), suifunephihaleirt indicator |
| 03 | Bromophenot Blue | pH dye | pH 3.0 (yellow) - pH 4.6 (blue), sulfonephthalein indicator |
| 04 | Bromophenol Red | pH dye | pH 5.2 (orange/yellow) - pH 6.8 (purple) |
| 05 | Bromothymo! Blue | pH dye | pH 6.0 (yellow) - pH 7.6 (blue), sulfonephthalein indicator |
| 06 | Brornoxylenol Blue | pH dye | pH 6.0 (yellow) - pH 7.6 (blue), sulfonephthalein indicator |
| 07 | Chlorophenol Red | pH dye | pH 4.8 (yellow) - pH 6.4 (red), sulfonephthalein indicator |
| 08 | m-Cresol Purple | pH dye | pH 1.2 - 2.8 (red-yellow) and pH 7.4-9.0 (yellow-purple), |
| 09 | Cresol Red | pH dye | pH 0.2 -1.8 (orange-yellow} and pH 7.2-8.8 (yellow -red/purple) |
| 10 | Litmus Soln | pH dye | Broad interval pH 4.8 (red) - pH 8.3 (blue), natural dye |
| 11 | Methyl red | pH dye | pH 4.2 (pink) - pH 6.2 (yellow), monoazo dye |
| 12 | Neutral Red | biological pH dye | pH 6.8 (red) - pH 8.0 (yellow), cationic azine dye |
| 13 | Nile Blue | pH, biological dye | pH 10.1 (blue) - pH 11.1 (red), cationic oxazme dye, stains nuclei blue, used as a lipid dye |
| 14 | Nitrazine Yellow | pH dye | pH 6.0 (bright yellow) - pH 7.2 (bright blue), anionic dye |
| 15 | Rosolic Acid | pH dye | pH 6.6 (yellow) - pH 8.0 (red) |
| 16 | Brilliant Blue E133 | Food colouring | |
| 17 | Fast Green FCFE143 | Food colouring | |
| 18 | Allura Red AC E129 | Food colouring | |
| 19 | Acid Red 1 | General dye | Anionic monoazo dye, used to dye fabric, paper, plastics etc, |
| 20 | Eriogi3UC:ne | Food colouring | Used to dye wool, silk, nylon, and paper. |
| 21 | Ponceau S Solution | Biological stain | Used as a protein stain, anionic diazo dye |

TABLE 1-continued

| No | Dye Name | Dye Type | Other |
|---|---|---|---|
| 22 | T3rtrazine | Synthetic food dye | Monoazo dye, used to dye foods, paper, wool contrast stain |
| 23 | Direct Blue 71 | Direct dye | Anionic triazo dye, used to dye cellulose, wool, paper etc. |
| 24 | Direct Red 23 | Direct dye | Anionic disazo dye, used to dye cotton, silk, paper etc. |
| 25 | Direct Violet 51 | Direct dye | Anionic disazo dye, used to dye cotton, silk, paper etc. |
| 26 | Acid Red 4 | General dye | Anionic dye, used to dye wool, nylon, paper etc. |
| 27 | Alcian Blue 8GX | Biological dye | Cationic dye, stain for polysaccharides, binds to negatively charged macromolecules, stains nuclei black. |
| 28 | Brilliant Blue G | Biological dye | Used to dye wool, silk, and paper, binds to proteins |
| 29 | Bromocresol Green | pH dye | pH 3.8 (yellow) - pH 5 4 (blue-green), sulfonephthalein |
| 30 | Chiorazol Fast Pink | Direct dye | Ansonic dis3zo dye, dyes cotton, silk, beater paper etc., |
| 31 | Coomassie Brilliant Blue R | Biological dye | Used to dye wool, silk and paper, binds to proteins |
| 32 | Crocein Orange G | General dye | Anionic monoazo dye, used to dye wool, silk, paper etc. |
| 33 | Fast Violet B | Textile dye | Used to dye cotton |
| 34 | Indigo Carmine | pH dye | pH 11.5 (blue) - pH 14.0 (yellow) |
| 35 | Indocyanine Green | Biological dye | Binds to plasma proteins, fluorescent dye |
| 35 | Methylene Blue | Biological stein | Can be used as a nuclear stain, antiseptic properties, |
| 37 | Mordant Blue 9 | General dye | Monoazo dye. used to stain wool, silk etc. |
| 38 | Oil Red 0 | Biological dye | Used as stain for lipids and fats |
| 39 | Orange G | pH dye | pH 11.5 (yellow) - pH 14.0 (pink), used to dye textiles, paper etc.. |
| 40 | Phthalocyanine Cu | Dye | Macrocyclic compound, used to dye textiles, papers etc. |
| 41 | Phihaloeyanine Green | Dye | Macrocyclic compound, used to dye textiles, papers etc., |
| 42 | Phthalocyanine Fe | Dye | Macrocyclic compound, used to dye textiles, papers etc. |
| 43 | Phthalocyanine Mg | Dye | Macrocyclic compound, used to dye textiles, papers etc. |
| 44 | Phthalocyanine Zn | Dye | Macrocyclic compound, used to dye textiles, papers etc. |
| 45 | Prussian Blue | Inorganic dye | Inorganic pigment., used to colour paints, textiles, paper |
| 46 | Reactive Blue 4 | Dye | Anthraquinone used to dye textiles |
| 47 | Rhodamine B | Fluorescent dye | Used to dye wool and cotton, biological stain for blood |
| 48 | Rhodamine 6G | Fluorescent dye | Used to dye paper, used as a laser dye |
| 49 | Ruthenium Red | Biological dye | Can be used as a biological stain for polysaccharides |

The invention claimed is:

1. A method to confirm successful EtO exposure wherein said method comprises:
   (a) exposing an article to EtO for a defined period of time wherein said article comprises an indicator;
   (b) inspecting a colour of said indicator following step (a); wherein said indicator comprises a solid support, a dye, and one or more nucleic acid stabilization chemicals, wherein said one or more nucleic acid stabilisation chemicals comprises a chaotrope, wherein the solid support is treated with the dye to form a chemical bond between the dye and the solid support, wherein the dye is selected from the group consisting of—
   (i) Bromophenol Red,
   (ii) Bromocresol Purple,
   (iii) Bromothymol Blue,
   (iv) Bromoxylenol Blue,
   (v) Chlorophenol Red,
   (vi) m-Cresol Purple,
   (vii) Cresol Red,
   (viii) Neutral Red,
   (ix) Nitrazine Yellow,
   (x) Rosolic Acid,
   (xi) Mordant Blue 9, and
   (xii) Ruthenium Red.

2. The method as defined in claim 1, wherein said solid support is selected from the group consisting of cellulose based paper and woven or non-woven fibrous materials, including man made, or naturally occurring polymer fibres or mineral fibre based materials.

3. The method as defined in claim 1, wherein said solid support is a cellulose based paper.

4. The method as defined in claim 1, wherein said solid support comprises more than one of said dyes.

5. The method as defined in claim 1, wherein said nucleic acid stabilisation chemicals further comprise a nucleic acid stabilisation chemical selected from the group consisting of a weak base, a chelating agent, an anionic surfactant, and an anti-oxidant.

6. The method as defined in claim 1, wherein said chaotrope is a guanidinium salt.

7. The method as defined in claim 1, wherein said article further comprises a label for attachment to said article intended for EtO treatment, wherein said label comprises (i) the indicator and (ii) means to fix said indicator to said article.

8. The method as defined in claim 1, wherein said defined period of time is 3-6 hours.

9. The method as defined in claim 1, wherein said defined period of time is effective for nucleic acid decontamination.

10. The method as defined in claim 9, wherein said article is the indicator.

11. The method as defined in claim 1, wherein said defined period of time is effective to sterilise said article.

* * * * *